(12) United States Patent
Markworth

(10) Patent No.: US 7,648,520 B2
(45) Date of Patent: Jan. 19, 2010

(54) PEDICLE SCREW ASSEMBLY

(75) Inventor: Aaron D. Markworth, Mountain View, CA (US)

(73) Assignee: Kyphon Sarl (CH)

( * ) Notice: Subject to any disclaimer, the term of this patent is extended or adjusted under 35 U.S.C. 154(b) by 544 days.

(21) Appl. No.: 10/825,962

(22) Filed: Apr. 16, 2004

(65) Prior Publication Data

US 2005/0234451 A1    Oct. 20, 2005

(51) Int. Cl.
*A61B 17/70*    (2006.01)

(52) U.S. Cl. ..................................... 606/246

(58) Field of Classification Search ........... 606/61, 606/250–253, 260, 266
See application file for complete search history.

(56) References Cited

U.S. PATENT DOCUMENTS

| | | | |
|---|---|---|---|
| 3,779,240 | A | 12/1973 | Kondo |
| 4,493,317 | A | 1/1985 | Klaue |
| 4,763,644 | A | 8/1988 | Webb |
| 4,805,602 | A | 2/1989 | Puno et al. |
| 4,946,458 | A | 8/1990 | Harms et al. |
| 5,005,562 | A | 4/1991 | Cotrel |
| 5,053,036 | A | 10/1991 | Perren et al. |
| 5,057,111 | A | 10/1991 | Park |
| 5,129,388 | A | 7/1992 | Vignaud et al. |
| 5,129,899 | A | 7/1992 | Small et al. |
| 5,147,361 | A | 9/1992 | Ojima et al. |
| 5,151,103 | A | 9/1992 | Tepic et al. |
| 5,171,279 | A | 12/1992 | Mathews |
| 5,176,678 | A | 1/1993 | Tsou |
| 5,176,679 | A | 1/1993 | Lin |
| 5,180,381 | A | 1/1993 | Aust et al. |
| 5,207,678 | A | 5/1993 | Harms et al. |
| 5,234,431 | A | 8/1993 | Keller |
| 5,246,442 | A | 9/1993 | Ashman et al. |
| 5,253,406 | A | 10/1993 | Shere et al. |
| 5,261,909 | A | 11/1993 | Sutterlin et al. |
| 5,269,784 | A | 12/1993 | Mast |
| 5,290,288 | A | 3/1994 | Vignaud et al. |
| 5,324,290 | A | 6/1994 | Zdeblick et al. |
| 5,360,431 | A | 11/1994 | Puno et al. |
| 5,395,371 | A | 3/1995 | Miller et al. |
| 5,429,639 | A | 7/1995 | Judet |

(Continued)

FOREIGN PATENT DOCUMENTS

DE    94 02 695.5 U1    4/1994

(Continued)

*Primary Examiner*—Thomas C Barrett
*Assistant Examiner*—Michael J Araj

(57) ABSTRACT

A medical device and methods of use thereof are provided for supporting a structure (e.g., bone). A screw assembly is provided that is comprised of a base, an arm, and an interconnection means for coupling the base to the arm. The interconnection means allows the arm to be positionable in a first position that is parallel to a long axis of the base and positionable in a second position that is perpendicular to the long axis of the base. The base is configured for attachment to a structure and the arm configured for attachment to a support structure. A support structure is provided that includes one or more receivers having locking means, which can be configured as an open-ended saddle for attachment to a medical device (e.g., a screw assembly). The support structure is configured to receive one or more medical devices and lock the medical devices to the support structure after installation in a patient.

35 Claims, 11 Drawing Sheets

U.S. PATENT DOCUMENTS

| | | | |
|---|---|---|---|
| 5,443,467 A | 8/1995 | Biedermann et al. | |
| 5,466,237 A | 11/1995 | Byrd, III et al. | |
| 5,466,238 A | 11/1995 | Lin | |
| 5,474,551 A * | 12/1995 | Finn et al. | 606/61 |
| 5,474,555 A | 12/1995 | Puno et al. | |
| 5,476,464 A | 12/1995 | Metz-Stavenhagen et al. | |
| 5,480,401 A | 1/1996 | Navas | |
| 5,480,440 A | 1/1996 | Kambin | |
| 5,499,983 A | 3/1996 | Hughes | |
| 5,501,684 A | 3/1996 | Schlapfer et al. | |
| 5,520,690 A | 5/1996 | Errico et al. | |
| 5,531,746 A | 7/1996 | Errico et al. | |
| 5,549,608 A | 8/1996 | Errico et al. | |
| 5,554,157 A | 9/1996 | Errico et al. | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,607,426 A | 3/1997 | Ralph et al. | |
| 5,609,593 A | 3/1997 | Errico et al. | |
| 5,647,873 A | 7/1997 | Errico et al. | |
| 5,649,926 A | 7/1997 | Howland et al. | |
| 5,669,911 A | 9/1997 | Errico et al. | |
| 5,672,176 A | 9/1997 | Biedermann et al. | |
| 5,733,285 A | 3/1998 | Errico et al. | |
| 5,733,286 A | 3/1998 | Errico et al. | |
| 5,817,094 A | 10/1998 | Errico et al. | |
| 5,876,403 A | 3/1999 | Shitoto et al. | |
| 5,882,350 A | 3/1999 | Ralph et al. | |
| 5,885,286 A | 3/1999 | Sherman et al. | |
| 5,951,553 A | 9/1999 | Betz et al. | |
| 5,964,761 A | 10/1999 | Kambin | |
| 5,964,988 A | 10/1999 | LaRose et al. | |
| 6,022,350 A | 2/2000 | Ganem | |
| 6,030,389 A | 2/2000 | Wagner et al. | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,113,601 A | 9/2000 | Tatar | |
| 6,280,442 B1 | 8/2001 | Barker et al. | |
| 6,296,644 B1 | 10/2001 | Saurat et al. | |
| 6,315,779 B1 | 11/2001 | Morrison et al. | |
| 6,585,738 B1 | 7/2003 | Mangione et al. | |
| 6,682,530 B2 | 1/2004 | Dixon et al. | |
| 6,736,817 B2 * | 5/2004 | Troxell et al. | 606/61 |
| 6,755,829 B1 | 6/2004 | Bono et al. | |
| 6,858,031 B2 | 2/2005 | Morrison et al. | |
| 6,884,241 B2 | 4/2005 | Bertranou et al. | |
| 6,887,241 B1 * | 5/2005 | McBride et al. | 606/61 |
| 7,220,262 B1 | 5/2007 | Hynes | |
| 2002/0007183 A1 * | 1/2002 | Lee et al. | 606/61 |
| 2002/0026194 A1 | 2/2002 | Morrison et al. | |
| 2003/0032957 A1 | 2/2003 | McKinley et al. | |
| 2003/0105460 A1 | 6/2003 | Crandall et al. | |
| 2003/0114853 A1 * | 6/2003 | Burgess et al. | 606/61 |
| 2003/0135210 A1 | 7/2003 | Dixon et al. | |
| 2004/0054371 A1 | 3/2004 | Dierks et al. | |
| 2004/0087949 A1 | 5/2004 | Bono et al. | |
| 2004/0092931 A1 | 5/2004 | Taylor et al. | |
| 2004/0127897 A1 | 7/2004 | Freid et al. | |
| 2004/0225290 A1 | 11/2004 | Ferree | |
| 2005/0038434 A1 | 2/2005 | Mathews | |
| 2005/0049588 A1 | 3/2005 | Jackson | |
| 2005/0101954 A1 * | 5/2005 | Simonson | 606/61 |
| 2005/0113927 A1 | 5/2005 | Malek | |
| 2005/0215999 A1 * | 9/2005 | Birkmeyer et al. | 606/61 |
| 2005/0234452 A1 | 10/2005 | Malandain | |
| 2005/0234456 A1 | 10/2005 | Malandain | |
| 2006/0149237 A1 * | 7/2006 | Markworth et al. | 606/61 |
| 2006/0149252 A1 | 7/2006 | Markworth et al. | |

FOREIGN PATENT DOCUMENTS

| | | |
|---|---|---|
| DE | 94 02 695 U1 | 4/1994 |
| FR | 2 780 631 | 1/2000 |
| WO | 00/54681 | 9/2000 |
| WO | 02/076315 | 10/2002 |
| WO | 2004/064603 | 8/2004 |
| WO | 2004/093701 | 11/2004 |

* cited by examiner

PEDICLE SCREW ASSEMBLY

TECHNICAL FIELD

This invention relates to medical devices.

BACKGROUND

The use of bone stabilization/fixation devices to align or position bones is well established. Furthermore, the use of spinal bone stabilization/fixation devices to align or position specific vertebrae or a region of the spine is well established. Typically such devices for the spine utilize a spinal fixation element, comprised of a relatively rigid member such as a plate, board or rod that is used as a coupler between adjacent vertebrae. Such a spinal fixation element can effect a rigid positioning of adjacent vertebrae when attached to the pedicle portion of the vertebrae using pedicle bone anchorage screws. Once the coupled vertebrae are spatially fixed in position, procedures can be performed, healing can proceed or spinal fusion may take place.

Spinal fixation elements may be introduced to stabilize the various vertebrae of the spine. Some devices for this purpose are designed to be attached directly to the spine, but the generally invasive nature of standard paraspinal approach used to implant these devices poses drawbacks. For example, the use of conventional pedicle screws and hooks is a relatively invasive protocol resulting in muscle disruption and blood loss.

SUMMARY

In general, in one aspect, the invention provides a medical device for supporting a structure comprising a screw assembly. The screw assembly includes a base, an arm, and an interconnection means for coupling the base to the arm. The interconnection means allows the arm to be positionable in a first position that is parallel to a long axis of the base and positionable in a second position that is perpendicular to the long axis of the base. The base is configured for attachment to a structure in a patient and the arm configured for attachment to a support structure. In one implementation, the structure attached to is bone.

The device can include a support structure and the screw assembly can be attached to the support structure by the arm. Alternatively, two screw assemblies can be attached to the support structure.

The screw assembly can be comprised of a material selected from the group consisting of titanium, stainless steel, carbon fiber, shape memory metal, a biocompatible material and a reabsorbable material and a composite or combination thereof. Alternatively, the screw assembly can be comprised of a continuous piece of shape memory metal. In one implementation the interconnection means is comprised of shape memory metal. In another implementation, the screw assembly, including the interconnection means is comprised of a piece of metal suited for bending.

The screw assembly can be of varying lengths, including an overall length in the range substantially between 0.1 and 100 centimeters. In one implementation, the overall length is in the range substantially between 50 and 600 millimeters. In another implementation, the screw assembly has an overall length sized for subcutaneous support of the spine. In yet another implementation, the screw assembly has an overall length sized for subcutaneous support of the posterior of a spine.

The arm of the screw assembly can be comprised of a body, a base yoke and a connector end. The body of the arm can be any of a number of shapes including rod shaped.

The base of the screw assembly can be comprised of a base head and an anchor. The anchor can be selected from the group consisting of a screw, staple, hook or nail. In one implementation the anchor is a screw configured for bone anchoring. In another implementation, the anchor is a screw configured for insertion into the pedicle of a vertebrae.

The interconnection means of the screw assembly can be of any of a number of configurations. In one implementation, the interconnection means includes a press-fit cross pin. In another implementation the interconnection means is comprised of an open saddle head and coupling-cross piece. The interconnection means can also include a setscrew, wherein the setscrew holds the arm and the base together as a single unit. Additionally, the setscrew can be tightened within the interconnection means to effect locking of the arm in a position that is substantially perpendicular to the long axis of the base. In another implementation, the locking means can also include a cam that can function analogously to the setscrew.

In one implementation, the device can be comprised of one screw assembly and a support structure, wherein the support structure includes a top surface, a bottom surface, an aperture and two receivers. In this implementation, the aperture can pass from the top surface through to the bottom surface of the support structure, wherein an anchor is disposed within the central aperture in an orientation substantially perpendicular to the top surface of the support structure.

The support structure of the device can be comprised of a top surface, a bottom surface and two receivers. Each receiver can include an open-ended saddle type receiver configured for attachment of one or more medical devices. Additionally, each receiver can include a locking means. The locking means can be a setscrew or cam. The locking means can be oriented within the plane of the top surface such that access to the locking means is from the top surface. The support structure can be configured to receive the medical devices and lock the medical devices to the support structure after the support structure has been installed.

The support structure can be comprised of a material selected from the group consisting of titanium, stainless steel, carbon fiber, a biocompatible material, a reabsorbable material and a composite or combination thereof. Additionally, the support structure can include a central aperture passing from the top surface through to the bottom surface of the support structure. An anchor can be disposed within the central aperture in an orientation substantially perpendicular to the top surface of the support structure. Alternatively, the support structure can include a central hinged claw having a threaded hinge-engagement member and nut disposed on the top surface. In use, tightening the nut onto the threaded hinge-engagement member causes a pivoting about the hinge to effect closing of the claw.

The device can be comprised of two screw assemblies and a support structure, wherein each screw assembly includes a base, an arm, and an interconnection means for coupling the base to the arm. The interconnection means allows the arm to be positionable in a first position that is parallel to a long axis of the base and positionable in a second position that is perpendicular to the long axis of the base. In this implementation, the base can be configured for attachment to a structure in a patient and the arm configured for attachment to the support structure. In one implementation, the structure attached to is bone. Additionally, the support structure can include a top surface, a bottom surface and two receivers, wherein each receiver includes an open-ended saddle type receiver configured for attachment to a medical device (e.g., screw assembly). The support structure can also include a locking means, to lock medical devices to the support structure after the support structure has been installed in a patient. The locking means can be setscrews or cams. Furthermore, the support structure in this implementation can include an anchor configured for attachment to a structure in a patient. In one implementation, the structure attached to in a patient is bone. Additionally, the anchor can be selected from the group consisting of a screw, staple, hook or a nail.

A method of use of the invention for supporting the spine, can include the steps of: 1) delivering to bone, two screw assemblies having arms, bases and interconnection means; 2) delivering to the vicinity of bone, a support structure having two receivers having locking means for the arms of the screw assemblies; 3) deploying the arms of the screw assemblies; and 4) engaging the locking means of the receivers to secure the arms of the screw assemblies to the support structure.

Another method of use of the invention for supporting the spine, can include the steps of: 1) delivering to bone, two screw assemblies having arms, bases and interconnection means; 2) delivering to bone, a support structure having a central aperture with a locking means and an anchor, and two receivers having locking means for the arms of the screw assemblies; 3) deploying the arms of the screw assemblies; and 4) engaging the locking means of the receivers to secure the arms of the screw assemblies to the support structure.

Yet another method of use of the invention for supporting the spine, can include the steps of: 1) delivering to bone, a screw assembly having an arm, base and interconnection means; 2) delivering to bone, a support structure having a central aperture with a locking means and an anchor, and a receiver having locking means for the arm of a screw assembly; 3) deploying the arm of the screw assembly; and 4) engaging the locking means of the receiver to secure the arm of the screw assembly to the support structure.

In a further implementation, the medical device support structure can include an anchor, a receiver, and a locking means; wherein the anchor is configured for attachment to a structure in a patient. The receiver can include an open end for attachment to a medical device (e.g., a screw assembly). The locking means can be configured to lock the medical device to the support structure, after the support structure has been deployed in a patient. In one implementation, the structure is bone. The locking means can be a setscrew or a cam. The anchor can be selected from the group consisting of a screw, staple, hook or nail. In another implementation, the receiver can include a plurality of receivers or openings for receiving medical devices.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
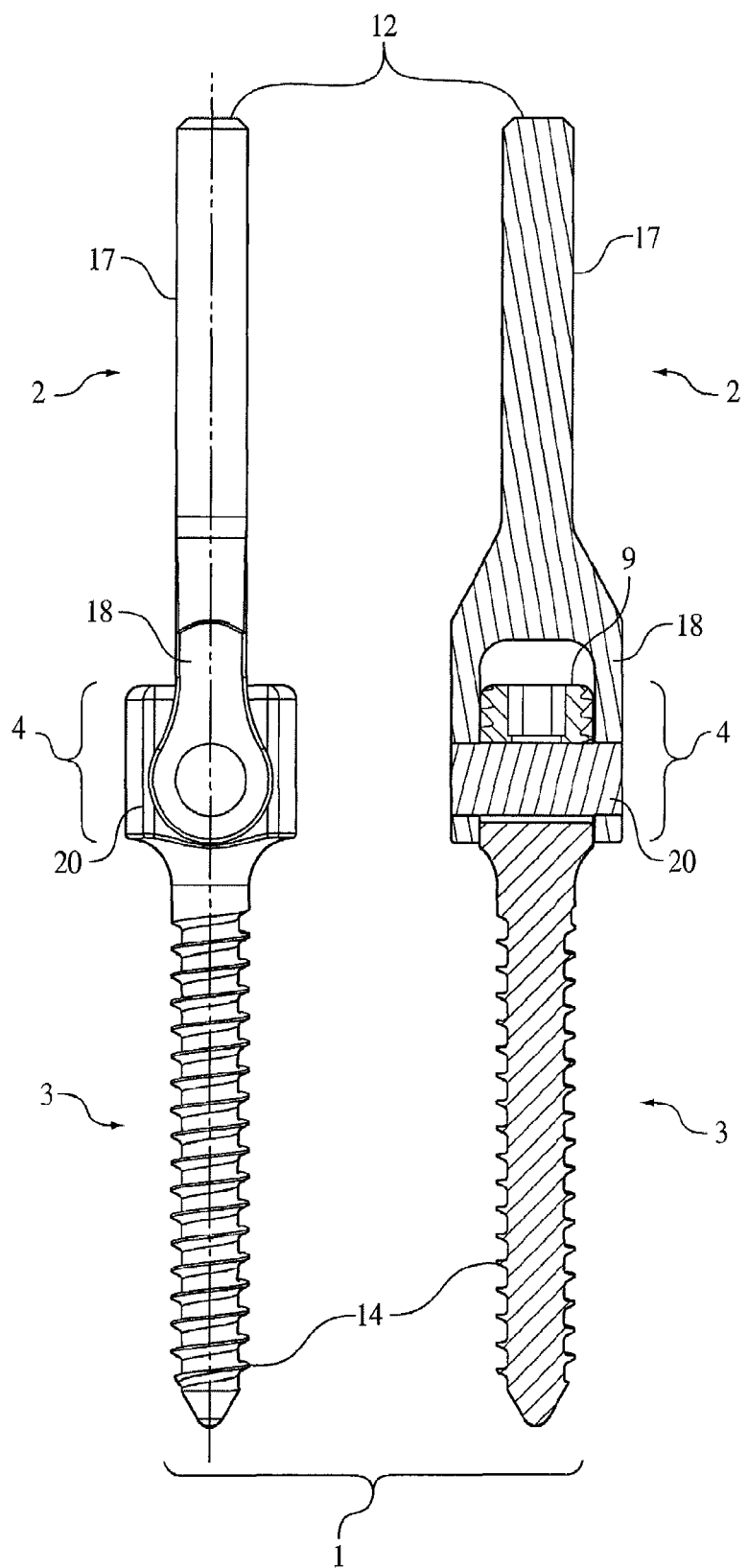
FIG. 1A is a drawing of a screw assembly showing the screw assembly, arm and base in a first position.
Figure 1B:
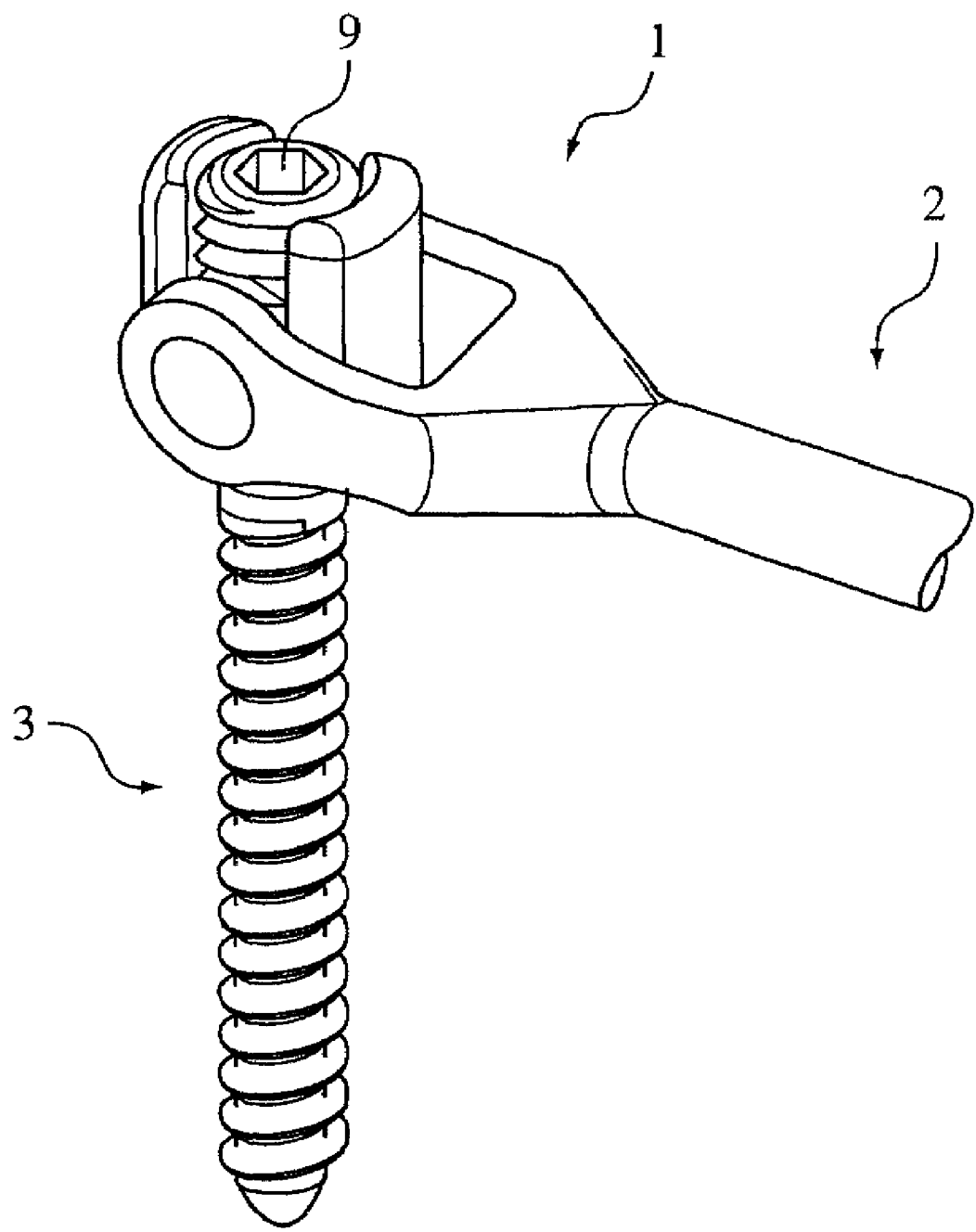
FIG. 1B is a drawing showing the screw assembly in a second position.

As shown in FIGS. 1A and 1B, a screw assembly 1 is provided comprised of an arm 2 and a base 3 in a single unit. The screw assembly 1 is elongate and the arm 2 and base 3 of the screw assembly 1, are coupled by an interconnection means 4. Additionally, as shown in FIGS. 1A and 1B, the interconnection means 4 facilitates movement between the arm 2 and the base 3, such that the arm 2 is positionable in a first position that is parallel to a long axis of the base 3 (shown in FIG. 1A) and positionable in a second position that is perpendicular to the long axis of the base 3 (shown in FIG. 1B). The base 3 of the screw assembly 1 is configured for attachment to a structure (e.g., a bone) and the arm 2 is configured for attachment to a support structure 10 (described in detail below). In application, one or more screw assemblies 1 are attached to a support structure 10. Preferably, two screw assemblies 1 are attached to a single support structure 10.

In an alternative screw assembly 1 implementation, the arm 2 and base 3 of the screw assembly 1 are configured as one continuous piece of shape memory metal. In this implementation, the interconnection means 4 is comprised of a shape memory metal that can facilitate movement of the arm 2 relative to the base 3 depending on preset conditions affecting the shape memory metal shape (not shown). In another alternative screw assembly 1 implementation, the arm 2 and base 3 of the screw assembly 1 are configured as one continuous piece wherein the interconnection means 4 between the arm 2 and base 3 is comprised of a material suited for bending (not shown).

Figure 7:
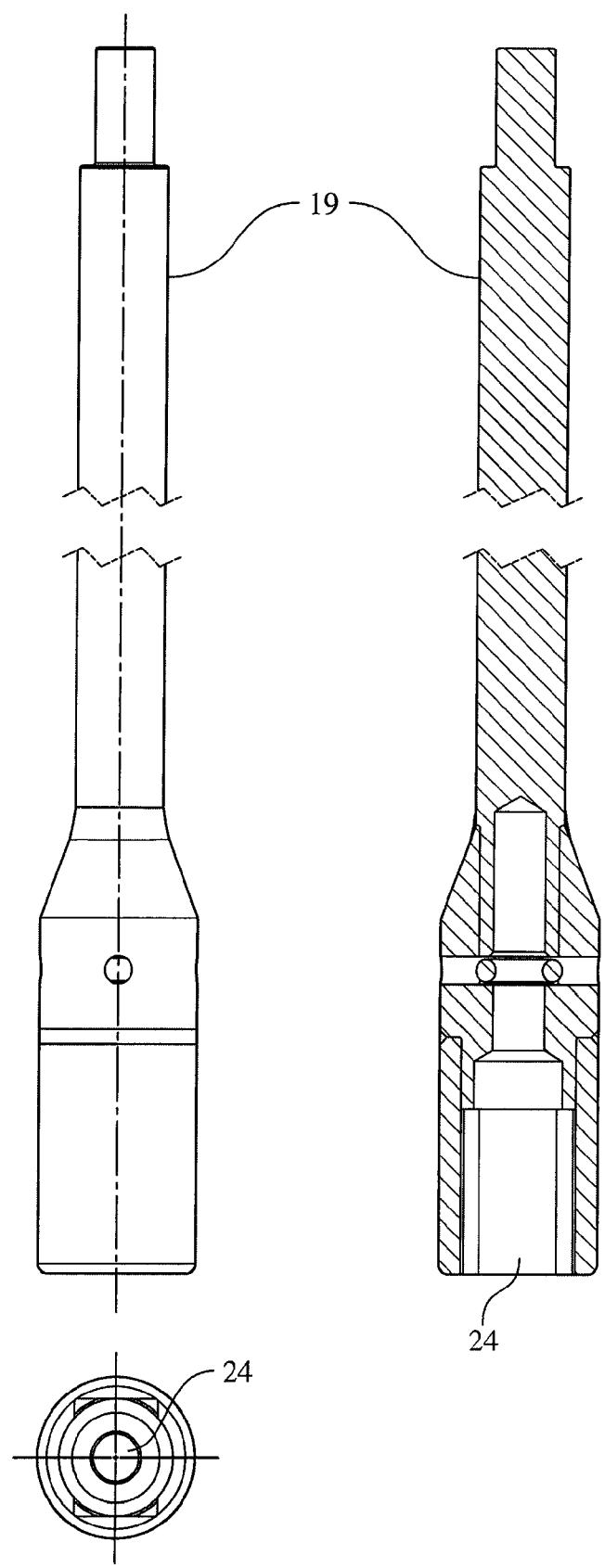
FIG. 7 is a drawing of a screw assembly tool used for manipulating the screw assembly during implantation of the screw assembly in the spine.

As shown in FIG. 1A, in certain embodiments, the arm 2 feature of the screw assembly 1 is comprised of a body 17, base yoke 18 and a connector end 12. The body 17 of the arm 2 can vary in shape and length with the application. In one implementation, the body 17 of the arm 2 is rod-shaped (see FIGS. 1A and 1B). Alternatively, the arm 2 body 17 is shaped to substantially fit within a screw assembly tool 19 for manipulating the screw assembly 1. An example of such a screw assembly tool 19 is illustrated in FIG. 7.

The screw assembly 1 can be made of numerous materials that are durable and that can be implanted in a body, including titanium, stainless steel, carbon fiber, biocompatible material, etc. In one implementation, the screw assembly 1 is made of titanium. Additionally, the screw assembly 1 can be made of a reabsorbable material or shape memory metal. Alternatively, the screw assembly 1 can be a composite or combination of any of the foregoing. The dimensions of the screw assembly 1 vary with the application. In general, the length of the screw assembly 1 is from 0.1 to 100 centimeters. In one implementation, the length is substantially between 50 and 600 millimeters. In another implementation, the screw assembly 1 is sized for applications involving support of the posterior of the spine 28 (see FIG. 3B).

As shown in FIG. 1A, the base 2 of the screw assembly 1 is comprised of a base head 20 and an anchor 14. The anchor 14 can be a screw, staple, hook or nail and can be of a type typically used for bone anchoring. In one implementation the anchor 14 is a screw of a type for insertion into a pedicle 26 of a vertebrae 27 (see FIGS. 1A and 3B).

Figure 1C:
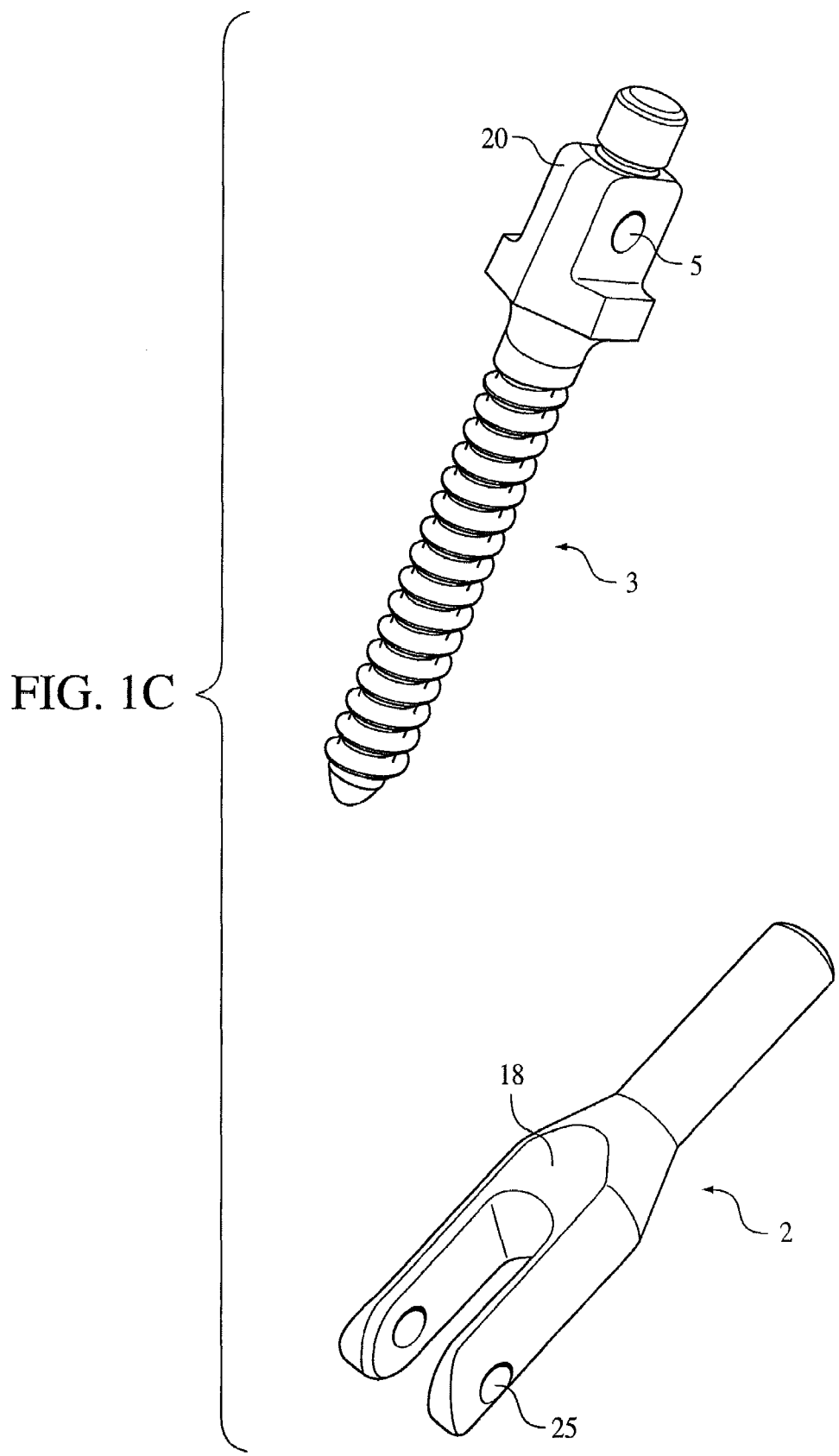
FIG. 1C is a drawing showing the screw assembly including a press-fit cross pin-type interconnection means.
Figure 1D:
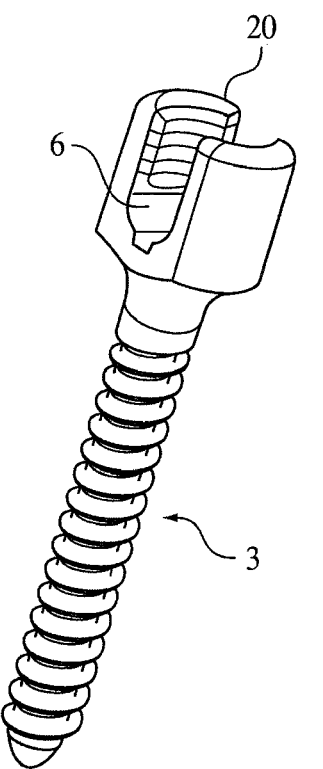
FIG. 1D is a drawing showing an open saddle-type base head.
Figure 1E:
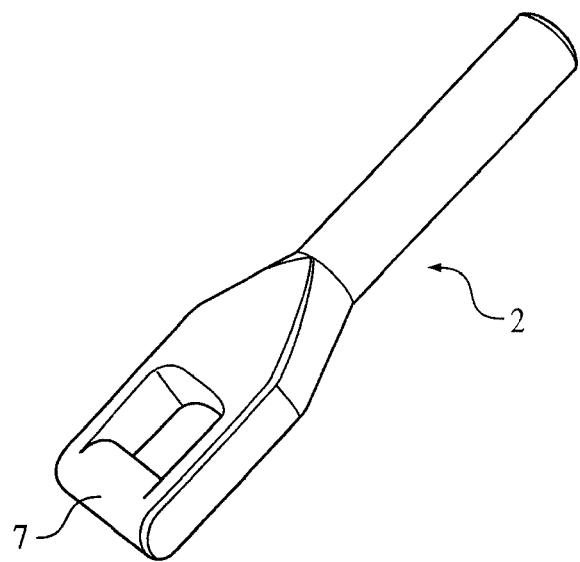
FIG. 1E is a drawing showing an integrally disposed crosspiece.
Figure 1F:
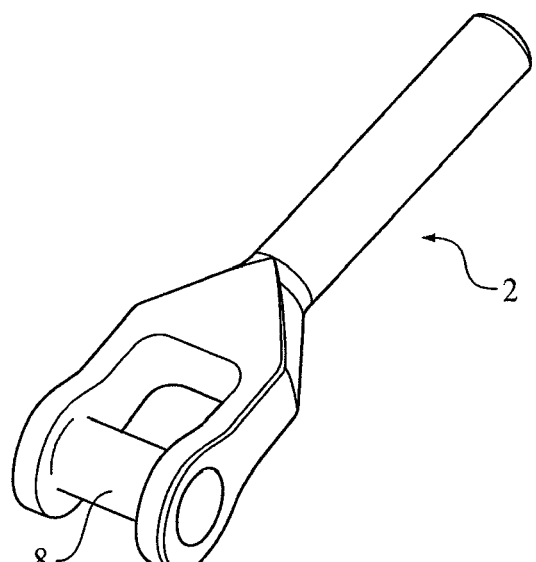
FIG. 1F is a drawing showing a press-fit cross pin.

As shown in FIG. 1C, the interconnection means 4 of the screw assembly 1 can be a press-fit cross pin type. In this implementation, the base head 20 is a press-fit cross pin-type head 5, and the yoke 18 of the arm 2 includes a pin hole 25, wherein the arm 2 and base 3 are pre-assembled including a press-fit cross pin (not shown) and a setscrew 9 (not shown). In an alternative implementation, as shown in FIGS. 1D-F, the interconnection means 4 is configured as an open saddle head with coupling-cross piece. In this implementation, the base head 20 is configured as an open saddle-type head 6 (shown in FIG. 1D), which is pre-assembled with a complementary arm 2 feature. As shown in FIG. 1E, the arm 2 feature that is complementary to the open saddle-type head 6 can be a one-piece integrally disposed crosspiece 7. Alternatively, as shown in FIG. 1F, the complementary arm 2 feature can be a press-fit cross pin 8.

As shown in FIGS. 1A and 1B, the arm 2 and base 3 can be held together as a single unit by the set screw 9 where the interconnection means 4 is of the form of a press-fit cross pin-type or an open saddle-type head 6 with a coupling cross piece. In certain implementations, the open saddle-type head 6 is threaded to receive the setscrew 9.

Additionally, as shown in FIGS. 1A and 1B, the setscrew 9 can effect locking of the arm 2 into a fixed position. Prior to moving the arm 2 into the deployed position, the setscrew 9 is loosely set in place. Upon deployment, the arm 2 can be locked in a position that is substantially perpendicular to the long axis of the base 3 by tightening the setscrew 9 into the threaded open saddle head 6 of the base 3 (see FIG. 1D).

In one implementation, locking of the arm 2 position and holding the arm 2 and base 3 together as a single unit can be achieved using a cam rather than a setscrew 9 (not shown). Where a cam is substituted for a setscrew 9, locking of the arm 2 and joining of the arm 2 and the base 3 is achieved by an analogous means.

Figure 2A:
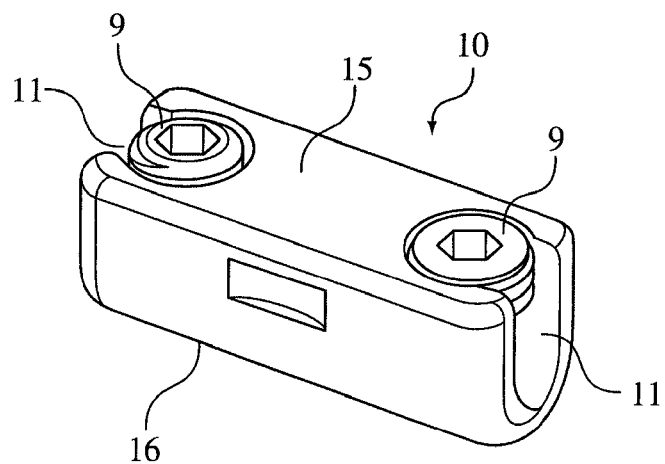
FIG. 2A is a drawing showing a support structure.
Figure 2B:
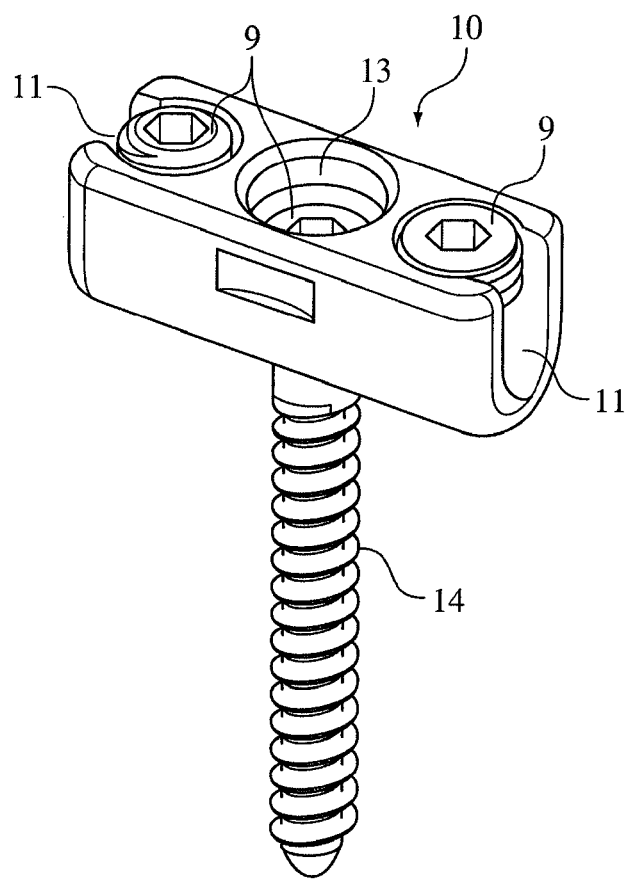
FIG. 2B is a drawing showing the support structure including a central aperture and an anchor.
Figure 2C:
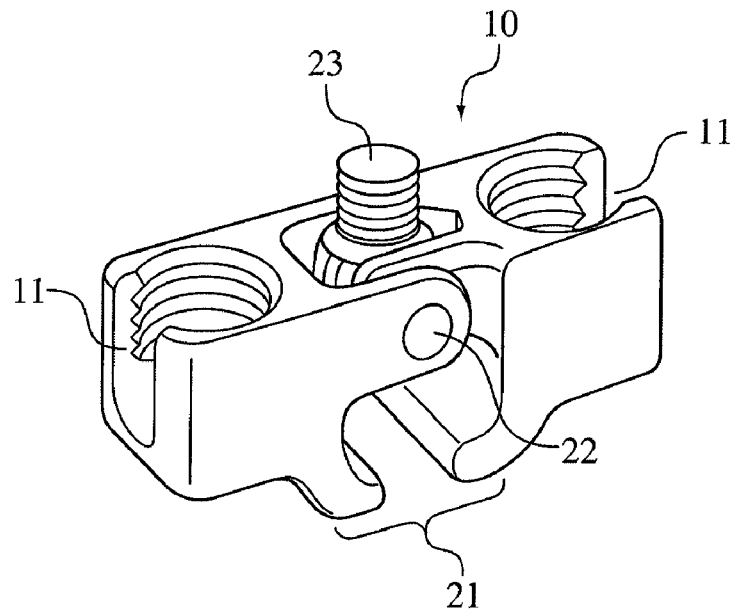
FIG. 2C is a drawing showing the support structure including a hinged claw.
Figure 3A:
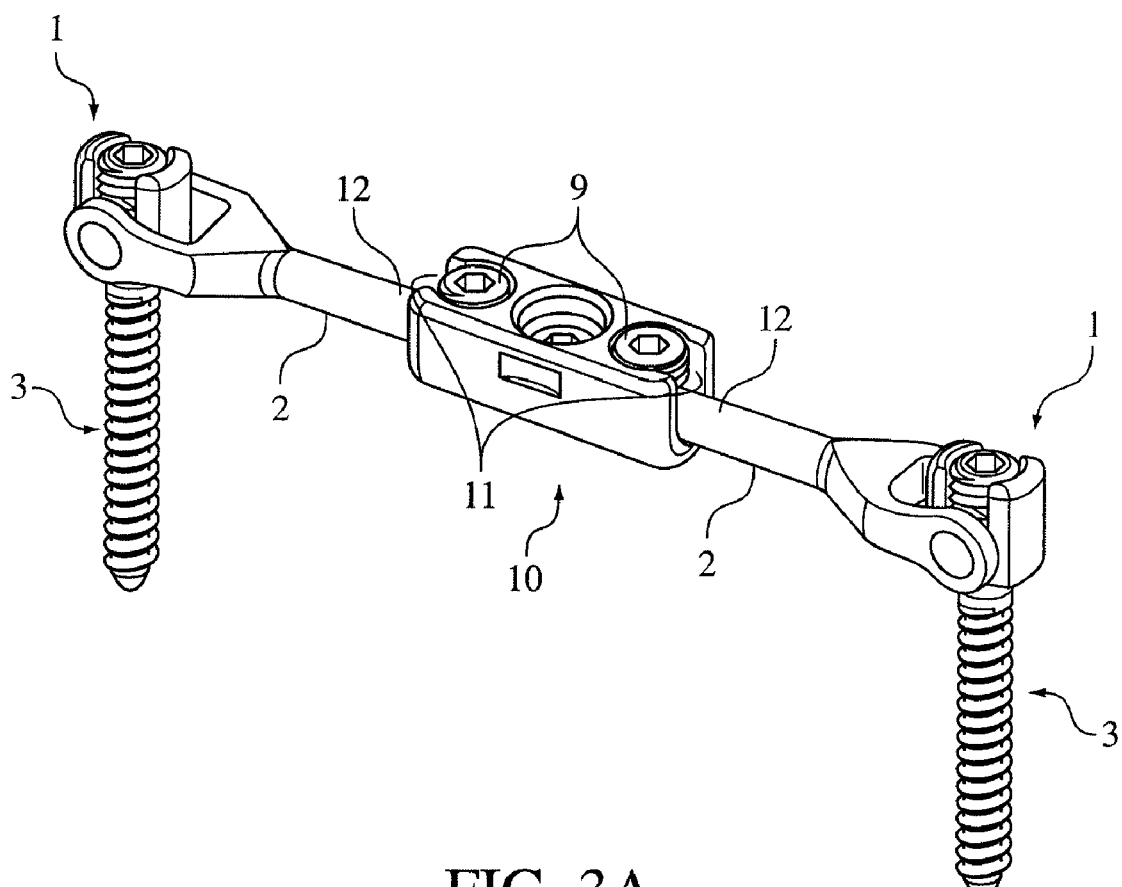
FIG. 3A is a drawing showing two screw assemblies connected by a support structure.
Figure 3B:
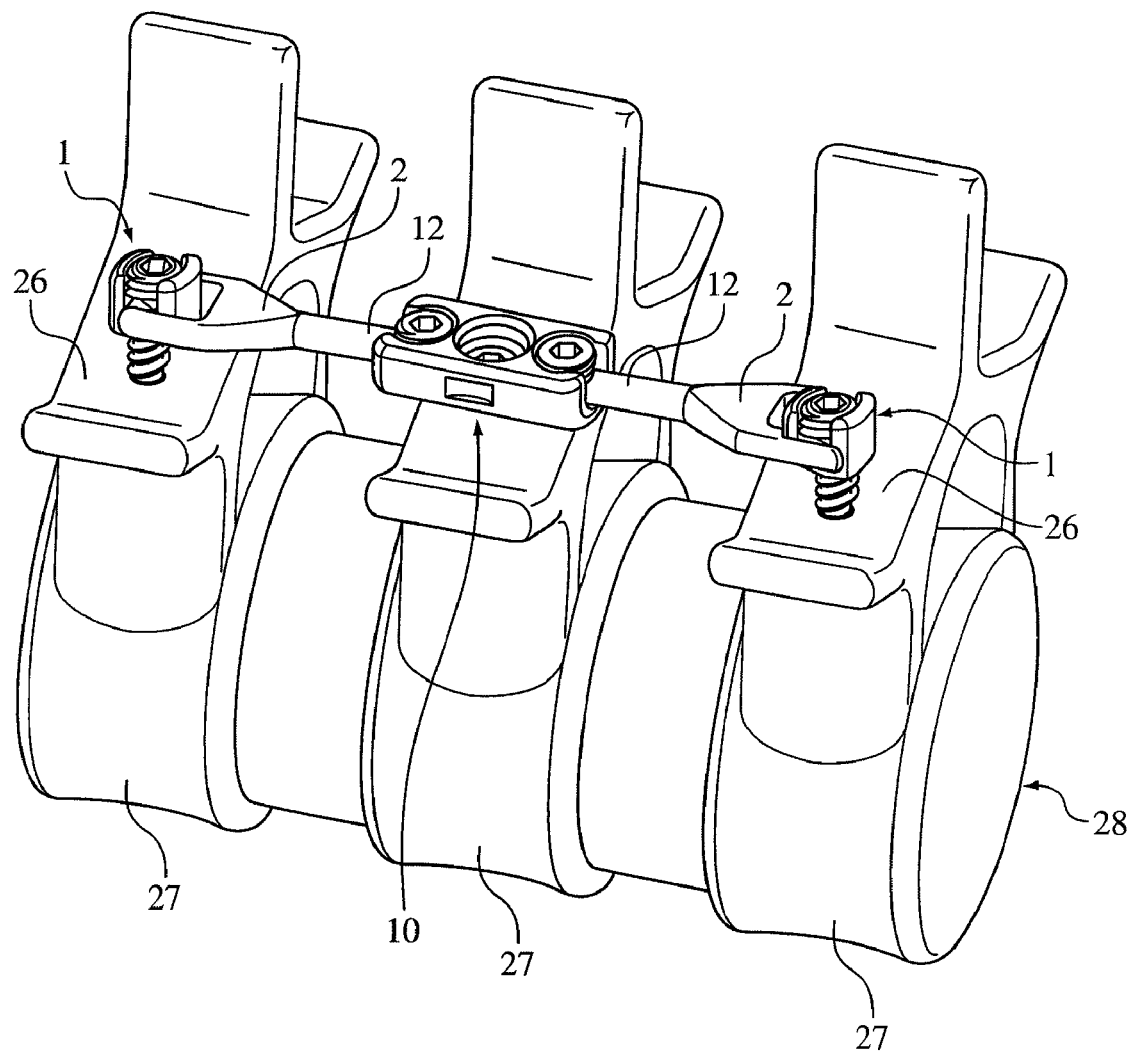
FIG. 3B is a drawing showing two screw assemblies connected by a support structure implanted into the pedicles of the vertebrae of the spine.
Figure 4:
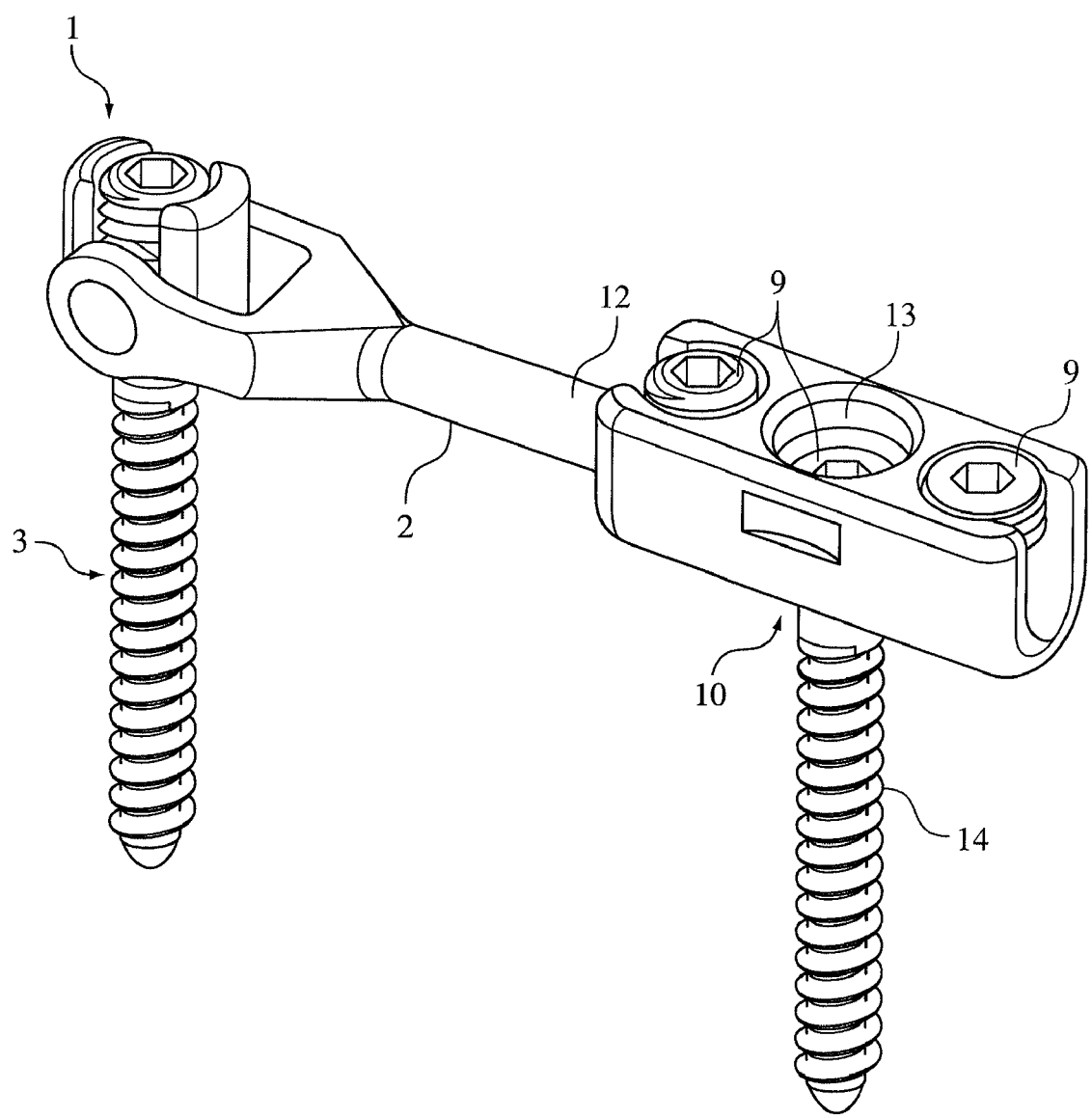
FIG. 4 is a drawing showing one screw assembly connected to a support structure having a central aperture and an anchor.

Referring now to FIGS. 2A-C, 3A, 3B and 4, a support structure 10 is shown to which the connector end 12 of the arm 2 of the screw assembly 1 can be attached (see FIGS. 3A, 3B and 4). As shown in FIG. 2A, the support structure 10 is comprised of a top surface 15, a bottom surface 16, and one or more open-ended saddle receivers 11 including a setscrew 9, or, in the alternative, a cam, for locking. The receiver 11 is shaped to accommodate the connector end 12 of the arm 2 of the screw assembly 1. As shown in FIGS. 2A and 2B, the setscrew 9 is threaded into the support structure 10, perpendicular to the plane of the top surface 15 of the support structure 10, to facilitate access to the setscrew 9 from above the support structure 10. In one implementation, the support structure 10 is comprised of two receivers 11 (see FIGS. 2A-C, 3A, 3B and 4), whereby two screw assemblies 1 can be linked together via the support structure 10 (see FIG. 3A). In another implementation, as shown in FIG. 3B, two screw assemblies 1 linked together via the support structure 10 can be implanted into the pedicles 26 of vertebrae 27 in a spine 28 to effect support of the spine 28.

As shown in FIGS. 2B and 4, the support structure 10 can be configured to additionally include a central aperture 13 that passes from the top surface 15 of the support structure 10 through to the bottom surface 16 of the support structure 10. As shown in FIGS. 2B and 4, the central aperture 13 can be threaded accommodate an anchor 14 and optionally include a setscrew 9 or a cam for locking the anchor 14 in position. In this implementation the threading of the central aperture 13, and receiver 11 setscrew(s) 9, are both aligned perpendicularly to the top surface 15 of the support structure 10. The anchor 14 can be a screw, staple, hook or nail and be of a type typically used for bone anchoring. In one implementation, the anchor 14 is a screw of a type for insertion into the pedicle 26 of a vertebrae 27.

In another implementation, as shown in FIG. 2C, the support structure 10 can optionally include a hinged claw 21 for clamping the support structure 10 onto a surface (e.g., a bony surface). The claw 21 features a hinge 22 positioned between two receivers 11 in the support structure 10. The claw 21 includes a threaded engagement member 23 extending above the top surface 15 of the support structure 10, whereby upon threading a nut (not shown) over the engagement member 23, a pivoting about the hinge 22 is effected and the claw 21 closes.

The support structure 10 can be made of numerous materials that are durable and that can be implanted within a body, including titanium, stainless steel, carbon fiber, biocompatible material, etc. Preferably, the screw assembly 1 is made of titanium. Additionally, the support structure 10 can be made of a reabsorbable material. Alternatively, the support structure 10 can be a composite or combination of any of the foregoing.

Figure 5:
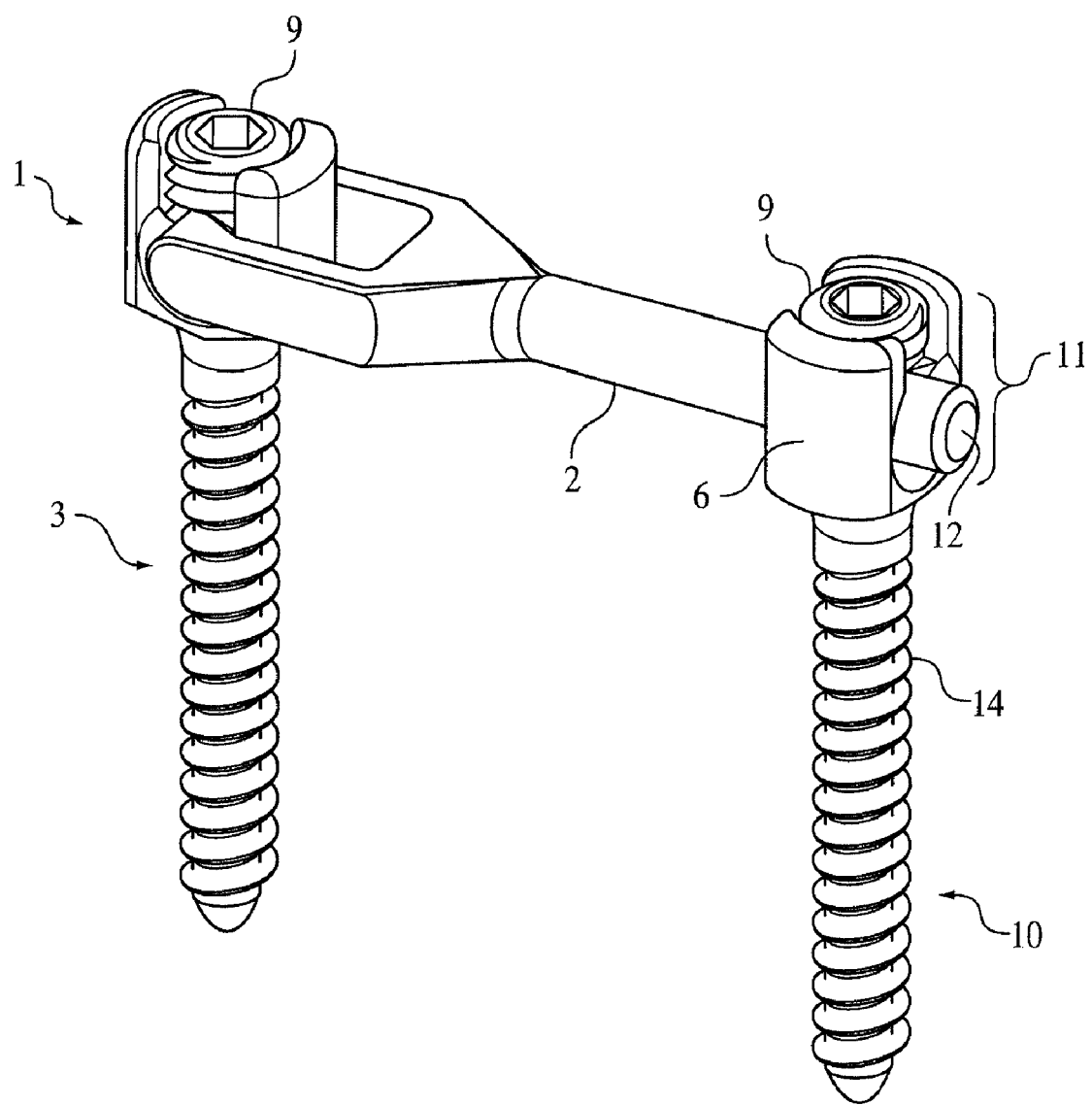
FIG. 5 is a drawing showing one screw assembly connected to a base having an open saddle-type head.

As shown in FIG. 5, another implementation of the invention includes a single screw assembly 1, connected to a support structure 10 having a receiver 11, an anchor 14 and a locking means. In one implementation the receiver 11 is configured as an open saddle-type head 6. In another implementation, the support structure 10 includes a plurality of receivers 11. The locking means can include a setscrew 9 or alternatively a cam. In one implementation, the connector end 12 of the screw assembly arm 2 is locked into the open saddle-type receiver head 6 of the support structure 10 after the anchor is installed in a patient.

Figure 6:
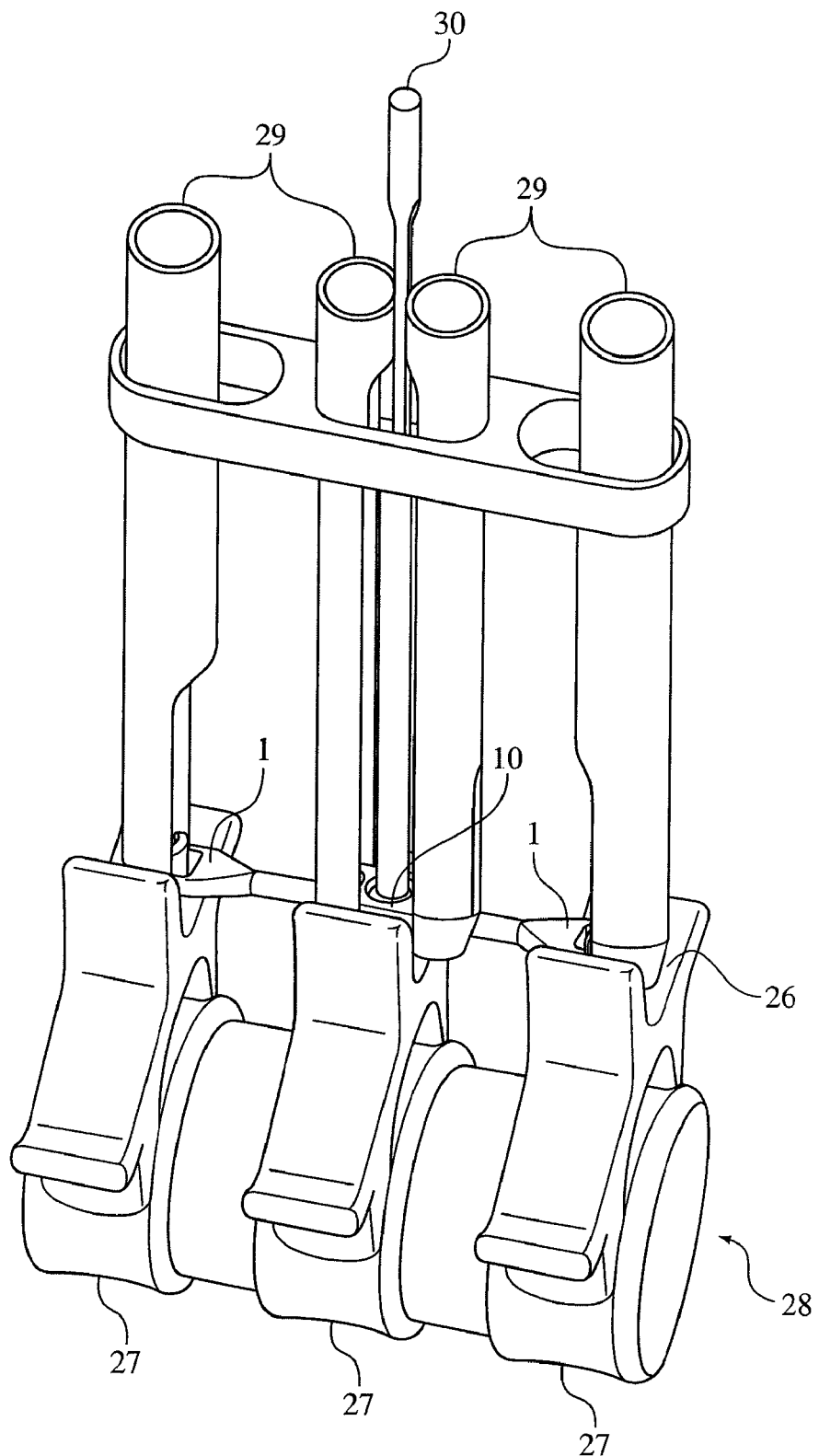
FIG. 6 is a drawing showing cannulas and a support structure tool used for implanting the screw assembly and support structure.

As shown in FIG. 6, a method of using the invention to support the spine 28 includes the steps of: 1) making a series of small incisions along the spine 28 to provide cannula 29 access to the pedicle 26 portions of a series of vertebrae 27; 2) using the cannula 29 access route, deliver two un-deployed screw assemblies 1 to a series of pedicles 26 and screw them into respective pedicles 26 (wherein un-deployed refers to a configuration of the screw assemblies 6 such that each arm 2 is set in a position that is parallel to the long axis of the base 3); 3) using the cannula 29 access route and a support structure tool 30, deliver, screw into place and lock a support structure 10 having a central aperture 13, set screw 9, two receivers 11 with setscrews 9 and pedicle screw-type anchor 4; 4) deploy the arms 2 of each screw assembly 1 substantially perpendicular to the long axis of the base 3; 5), and engage and lock into place each connector end 12 of each arm 2 within the support structure 10 receivers 11 using the set screws 9.

The above method includes the use of a special screw assembly tool 19 for manipulation of the screw assemblies 1

(see FIG. 7). The screw assembly tool 19 includes an inner cavity 24 configured to accommodate the un-deployed screw assembly 1 within it. In use, the screw assembly tool 19 facilitates the insertion of the un-deployed screw assembly 1 base 3 into a structure (e.g., bone) from within the confines of a cannula 29.

An additional method of use of the invention for supporting the spine, can include the steps of: 1) delivering to bone, two screw assemblies 1 having arms 2, bases 3 and interconnection means 4; 2) delivering to the vicinity of bone, a support structure 10 having two receivers 11 having locking means for the arms 2 of the screw assemblies 1; 3) deploying the arms 2 of the screw assemblies 1; and 4) engaging the locking means of the receivers 11 to secure the arms 2 of the screw assembly 1 to the support structure 10.

Another method of use of the invention for supporting the spine, can include the steps of: 1) delivering to bone, two screw assemblies 1 having arms 2, bases 3 and interconnection means 4; 2) delivering to bone, a support structure 10 having a central aperture 13 with a locking means and an anchor 14, and two receivers 11 having locking means for the arms 2 of the screw assemblies 1; 3) deploying the arms 2 of the screw assemblies 1; and 4) engaging the locking means of the receivers 11 to secure the arms 2 of the screw assemblies 1 to the support structure 10.

Yet another method of use of the invention for supporting the spine, can include the steps of: 1) delivering to bone, a screw assembly having an arm, base and interconnection means; 2) delivering to bone, a support structure having a central aperture with a locking means and an anchor, and a receiver having locking means for the arm of a screw assembly; 3) deploying the arm of the screw assembly; and 4) engaging the locking means of the receiver to secure the arm of the screw assembly to the support structure.

The method of supporting the spine can also be used in conjunction with a kyphoplasty procedure. Kyphoplasty is a percutaneous technique involving the use of an expandable structure, such as a balloon catheter, to create a cavity or void within the vertebral body, followed by filling the cavity with a bone substitute to form an "internal cast". Methods and instruments suitable for such treatment are more fully described in U.S. Pat. Nos. 4,969,888 and 5,108,404, which are incorporated herein by reference. Kyphoplasty can be used to reduce vertebral compression fractures and to move bone with precision, thus restoring as close to normal the natural alignment of the vertebral column. Reduction of traumatic vertebral compression fractures have historically been treated with open reduction, internal fixation stabilization hardware and fusion techniques using a posterior approach. The usual role of stabilization hardware is to stop motion across the disk so that bone graft can fuse one vertebral body to the next. Usually, the stabilization hardware is left in permanently. In trauma repair, stabilization hardware is used to offload the fractured vertebral body so that the natural healing process can occur. In trauma, the stabilization hardware is designed to facilitate easy removal. Stabilization hardware can take many forms, including those described herein. The combination of kyphoplasty and insertion of stabilization hardware utilizing the naturally occurring interior muscle plane as described in Wiltse and Spencer, Spine (1988) 13(6): 696-706, satisfies the goals of improving the quality of patient care through minimally invasive surgical therapy.

A number of preferred embodiments of the invention have been described. Nevertheless, it will be understood that various modifications may be made without departing from the spirit and scope of the invention. For example, while the some implementations have been described using screws to anchor into bony structures, the scope of the invention is not so limited. Any means of anchoring can be used, such as a cam, screw, staple, nail, pin, or hook. Accordingly, other embodiments are within the scope of the following claims.

What is claimed is:

1. A medical device for supporting a structure comprising:
   a screw assembly, the screw assembly including
      a base,
      an arm,
      an interconnection means for coupling the base to the arm, the interconnection means including a press-fit cross pin extending from the arm through the base allowing the arm to be positionable in a first position that is parallel to a long axis of the base and positionable in a second position that is perpendicular to the long axis of the base, wherein the interconnection means is comprised of a setscrew,
      wherein the setscrew maintains the arm and the base together as a single unit;
      wherein the setscrew can be tightened within the interconnection means to effect locking of the arm in a position that is substantially perpendicular to the long axis of the base,
      where the base is configured for attachment to a first structure in a patient and the arm is configured for attachment to a support structure;
   the support structure, comprising:
      a support element configured to support a second structure in the patient, at least one receiver included in the support element and configured to receive the arm of the screw assembly, and
      a locking mechanism configured to lock the arm to the support element.

2. The medical device of claim 1, wherein the first structure in the patient is bone.

3. The medical device of claim 1, further comprising a second screw and wherein the first and second screw assemblies are attached to the support structure, the support structure including two receivers.

4. The medical device of claim 1, wherein the screw assembly is comprised of a material selected from the group consisting of titanium, stainless steel, carbon fiber, shape memory metal, a biocompatible material, a reabsorbable material, and combinations and composites thereof.

5. The medical device of claim 1, wherein the screw assembly is comprised of titanium.

6. The medical device of claim 1, wherein the screw assembly is comprised of a continuous piece of shape memory metal.

7. The medical device of claim 1, wherein the interconnection means is comprised of shape memory metal.

8. The medical device of claim 1, wherein the screw assembly is comprised of a continuous piece of material suited for bending; and wherein the interconnection means for coupling the base to the arm is positioned by bending.

9. The medical device of claim 1, wherein the screw assembly has an overall length in the range substantially between 0.1 and 100 centimeters.

10. The medical device of claim 1, wherein the screw assembly has an overall length in the range substantially between 50 and 600 millimeters.

11. The medical device of claim 1, wherein the screw assembly has an overall length sized for subcutaneous support of the posterior of a spine.

12. The medical device of claim 1, wherein the arm is comprised of a body having a distal end and a proximal end, a base yoke positioned at the proximal end and a connector positioned at the distal end.

13. The medical device of claim 12, wherein the body of the arm is rod shaped.

14. The medical device of claim 1, wherein the base is comprised of a base head coupled to the arm and an anchor.

15. The medical device of claim 14, wherein the anchor is selected from the group consisting of a screw, staple, hook and a nail.

16. The medical device of claim 15, wherein the anchor is a screw configured for bone anchoring.

17. The medical device of claim 16, wherein the anchor is a screw configured for insertion into the pedicle of a vertebrae.

18. The medical device of claim 1, wherein the interconnection means is comprised of an open saddle head.

19. The medical device of claim 1, further the support structure further comprising:
   an anchor connected to the support element,
   wherein the anchor is configured for attachment to the second structure in the patient.

20. A medical device for supporting a structure comprising:
   a screw assembly, the screw assembly including
      a base,
      an arm,
      an interconnection means for coupling the base to the arm, the interconnection means including a press-fit cross pin extending from the arm through the base allowing the arm to be positionable in a first position that is parallel to a long axis of the base and positionable in a second position that is perpendicular to the long axis of the base,
   wherein the interconnection means is comprised of a cam;
      wherein the cam maintains the arm and the base together as a single unit;
      wherein the cam can be turned within the interconnection means to effect locking of the arm in a position that is substantially perpendicular to the long axis of the base,
      where the base is configured for attachment to a first structure in a patient and the arm is configured for attachment to a support structure;
   the support structure, comprising:
      a support element configured to support a second structure in the patient,
      at least one receiver included in the support element and configured to receive the arm of the screw assembly, and
   a locking mechanism configured to lock the arm to the support element.

21. A medical device support structure comprising:
   two receivers;
   wherein each receiver includes
   an open-ended receiver configured for attachment to a medical device and
   a locking means, the support structure configured to receive the medical devices and lock the medical devices to the support structure using the locking means, after the support structure has been installed in a patient; and
   a hinged claw having a threaded hinge-engagement member and nut disposed on a top surface of the medical device support structure.

22. The medical device support structure of claim 21, wherein the open-ended receiver is configured as a saddle-type receiver.

23. The medical device support structure of claim 21, wherein the locking means is selected from the group consisting of a setscrew and a cam.

24. The medical device support structure of claim 21, wherein the locking means are oriented within a plane of a top surface of the medical device support structure for access from the top surface.

25. The medical device support structure of claim 21, wherein the support structure is comprised of a material selected from the group consisting of titanium, stainless steel, carbon fiber, a biocompatible material, a reabsorbable material and combinations and composites thereof.

26. The medical device support structure of claim 21, wherein the medical device support structure is comprised of titanium.

27. The medical device support structure of claim 21, wherein the hinged claw is a central hinged claw and tightening the nut onto the threaded hinge-engagement member causes a pivoting about the hinge to effect closing of the claw.

28. The medical device support structure of claim 21, further comprising:
   two screw assemblies;
   wherein each screw assembly includes
      a base,
      an arm, and
      an interconnection means for coupling the base to the arm, the interconnection means allowing the arm to be positionable in a first position that is parallel to a long axis of the base and positionable in a second position that is perpendicular to the long axis of the base, the base configured for attachment to a first structure in a patient and the arm configured for attachment to the support structure.

29. The medical device support structure of claim 28, wherein the first structure in a patient is bone.

30. The medical device support structure of claim 28, wherein the support structure further comprises:
   an anchor and
   a locking means for the anchor;
   wherein the anchor is configured for attachment to a structure in a patient.

31. The medical device support structure of claim 30 wherein the second structure in a patient is bone.

32. The medical device support structure of claim 30 wherein the locking means is selected from the group consisting of a setscrew and a cam.

33. The medical device support structure of claim 30 wherein the anchor is selected from the group consisting of a screw, staple, hook and a nail.

34. A medical device for supporting a structure comprising:
   a screw assembly, the screw assembly including
      a base,
      an arm, and
      an interconnection means for coupling the base to the arm, the interconnection means allowing the arm to be positionable in a first position that is parallel to a long axis of the base and positionable in a second position that is perpendicular to the long axis of the base, wherein the interconnection means is comprised of an open saddle head, coupling-cross piece, and a setscrew, wherein the setscrew maintains the arm and the base together as a single unit, and wherein the setscrew can be tightened within the interconnection means to effect locking of the arm in a position that is substantially perpendicular to the long axis of the base, where the base is configured for attachment to a first structure in a patient and the arm configured for attachment to a support structure; and the support structure, comprising:

a support element configured to support a second structure in the patient, at least one receiver included in the support element and configured to receive the arm of the screw assembly, and a locking mechanism configured to lock the arm to the support element.

35. A medical device for supporting a structure comprising:

a screw assembly, the screw assembly including
a base,
an arm, and
an interconnection means for coupling the base to the arm, the interconnection means allowing the arm to be positionable in a first position that is parallel to a long axis of the base and positionable in a second position that is perpendicular to the long axis of the base, wherein the interconnection means is comprised of an open saddle head, a coupling-cross piece, and a cam, wherein the cam maintains the arm and the base together as a single unit, and wherein the cam can be turned within the interconnection means to effect locking of the arm in a position that is substantially perpendicular to the long axis of the base where the base is configured for attachment to a first structure in a patient and the arm configured for attachment to a support structure; and the support structure, comprising:

a support element configured to support a second structure in the patient, at least one receiver included in the support element and configured to receive the arm of the screw assembly, and a locking mechanism configured to lock the arm to the support element.

* * * * *

UNITED STATES PATENT AND TRADEMARK OFFICE
CERTIFICATE OF CORRECTION

PATENT NO.        : 7,648,520 B2  
APPLICATION NO. : 10/825962  
DATED             : January 19, 2010  
INVENTOR(S)      : Aaron D. Markworth Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 978 days.

Signed and Sealed this

Twenty-third Day of November, 2010

David J. Kappos  
*Director of the United States Patent and Trademark Office*